United States Patent
Fritz et al.

(10) Patent No.: US 7,895,880 B2
(45) Date of Patent: Mar. 1, 2011

(54) PHOTOACOUSTIC CELL INCORPORATING A QUANTUM DOT SUBSTRATE

(75) Inventors: Bernard S. Fritz, Eagan, MN (US); Matthew S. Marcus, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 254 days.

(21) Appl. No.: 12/105,241

(22) Filed: Apr. 17, 2008

(65) Prior Publication Data

US 2009/0320561 A1    Dec. 31, 2009

(51) Int. Cl.
 *G01N 21/61* (2006.01)
 *G01N 29/02* (2006.01)
(52) U.S. Cl. .................. 73/24.02; 356/432; 356/437
(58) Field of Classification Search ............... 73/24.01, 73/24.02; 356/432, 433, 437
 See application file for complete search history.

(56) References Cited

U.S. PATENT DOCUMENTS

| 4,457,162 A | 7/1984 | Rush et al. |
| 5,933,245 A | 8/1999 | Wood et al. |
| 2002/0093658 A1 * | 7/2002 | Han .............................. 356/432 |
| 2007/0221867 A1 | 9/2007 | Beeson et al. |
| 2008/0173886 A1 * | 7/2008 | Cheon et al. ................... 257/98 |
| 2008/0204383 A1 * | 8/2008 | McCarthy et al. .............. 345/83 |
| 2008/0246017 A1 * | 10/2008 | Gillies et al. ................... 257/13 |

FOREIGN PATENT DOCUMENTS

| EP | 1111367 A2 | 6/2001 |
| EP | 1857789 A2 | 11/2007 |
| JP | 2006323410 | 11/2006 |

OTHER PUBLICATIONS

"European Application No. 09157446.7, European Search Report Mailed Dec. 8, 2009", 8 pgs.

* cited by examiner

*Primary Examiner*—Lisa M Caputo
*Assistant Examiner*—Punam Roy
(74) *Attorney, Agent, or Firm*—Schwegman, Lundberg & Woessner P.A.

(57) ABSTRACT

Embodiments of the apparatus, systems, and methods relate to a photoacoustic cell including an excitation source, a chamber, and a quantum dot substrate between the excitation source and the chamber. The excitation source generates a light spectrum. The quantum dot substrate, when subjected to the light spectrum, emits a specific wavelength of light to be received by the chamber. The photoacoustic cell apparatus may be part of a portable gas sensing system, and may be used to detect and measure the concentration of one or more gases. Additional apparatus, systems, and methods are disclosed.

20 Claims, 3 Drawing Sheets

PHOTOACOUSTIC CELL INCORPORATING A QUANTUM DOT SUBSTRATE

TECHNICAL FIELD

The subject matter relates generally to photoacoustic or optoacoustic spectroscopy and, more particularly, to a photoacoustic cell, and to operating methods related thereto.

BACKGROUND

Photoacoustic measurement is based on the tendency of molecules in a gas, when exposed to certain wavelengths of radiant energy (e.g. infrared light), to absorb the energy and reach higher levels of molecular vibration and rotation, thereby reaching a higher temperature and pressure within a measurement cell. When the radiant energy striking a gas is amplitude modulated at a known frequency, the resulting fluctuations in energy available for absorption produce corresponding temperature and pressure fluctuations in the gas, which can be measured as an acoustic signal. The amplitude of the acoustic signal is proportional to the intensity of the radiation and the concentration value of the absorbing gas. Such devices are well suited for measuring small concentration values of gases (i.e., in the parts-per-billion range).

Prior art photoacoustic measurement devices have several components in common. In particular, an energy source produces radiant energy which is modulated at a known frequency either thermally (power on/off) or with a chopping device. The modulated energy is provided to a cell containing a gas that absorbs the radiant energy leading to temperature fluctuations in the gas that track the modulation frequency. Temperature is not sensed directly. Rather, pressure fluctuations that accompany the temperature fluctuations are detected by a sensitive microphone in the cell. The microphone output is detected at the modulation frequency, to provide an electrical signal proportional to gas concentration.

DETAILED DESCRIPTION

Figure 1:
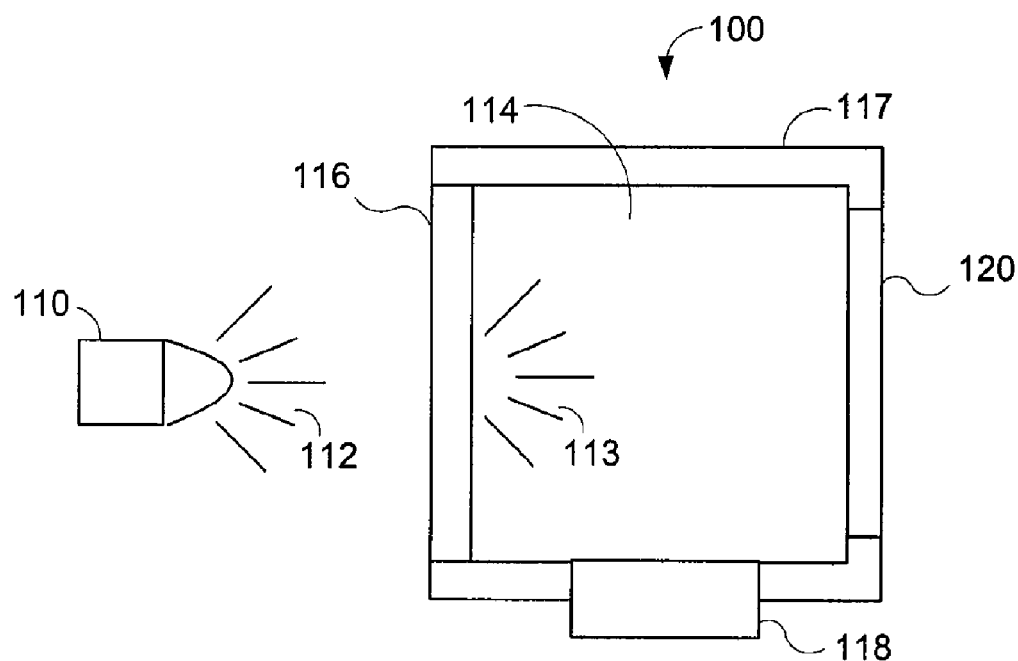
FIG. 1 illustrates a photoacoustic cell incorporating a quantum dot substrate.

In the following detailed description of embodiments of the subject matter, reference is made to the accompanying drawings, which form a part hereof, and in which is shown by way of illustration some embodiments in which the subject matter may be practiced. These embodiments are described in sufficient detail to enable those skilled in the art to practice the subject matter, and it is to be understood that other embodiments may be utilized and that structural, mechanical, compositional, electrical, and procedural changes may be made without departing from the spirit and scope of the subject matter. The following detailed description is, therefore, not to be taken in a limiting sense, and the scope of the subject matter is defined only by the appended claims.

"Suitable", as used herein, means having characteristics that are sufficient to produce the desired result(s). Suitability for the intended purpose can be determined by one of ordinary skill in the art using only routine experimentation.

The subject matter provides a solution to certain acoustic background noise and power consumption problems that are associated with prior art photoacoustic gas sensors.

Gas sensors based on the absorption of photons by the gas of interest, such as the photoacoustic sensing method, require a modulatable infrared (IR) radiation source that emits at the absorption band of the gas to be detected. Current technology on the market cannot create a low cost, low power, modulatable IR source for use in gas absorption detectors. Previous attempts at manufacturing a low cost photoacoustic sensor have utilized an incandescent lamp with an optical interference filter in order to create a modulatable narrow waveband IR source. However, an IR source using an incandescent lamp requires a large amount of electrical power, which is impractical in many circumstances, and the interference filter can be cost prohibitive. An IR source using an incandescent lamp has a limited maximum wavelength that can be produced, due to IR absorption by the glass or other material enclosing the lamp filament. Additionally, the modulation of an incandescent IR source is limited to approximately 8-10 Hz, and as a result, a photoacoustic sensor utilizing such a source is extremely susceptible to background acoustic noise interference, and a resonant cavity design is impractical. An IR source consisting of an IR light emitting diode (LED) or IR laser becomes more expensive, and eventually cost prohibitive, as the wavelength approaches 2-5 micrometers and longer.

An IR source based on the fluorescence of quantum dots allows modulation to kHz levels and higher and does not require an optical interference filter. Higher IR source modulation frequencies yield a better signal to noise ratio and reduced sensitivity to background noise. The power required for a quantum dot IR source is significantly lower than that for an incandescent source producing comparable IR radiation. Additionally, a quantum dot IR source may produce longer wavelengths of IR radiation at a significantly lower cost than is currently possible with other methods, thereby allowing low-cost portable photoacoustic sensors to be produced.

In an embodiment, a quantum dot substrate, located between an LED and a chamber, emits a specific wavelength to be received by the chamber. The LED may be modulated at a frequency between 20 and 40 kilohertz (kHz). The specific wavelength emitted by the quantum dot substrate may be between 1 and 4 microns, with the possibility of extending further into the infrared. Various embodiments are illustrated and described herein, including methods of operation, as well as application of the subject matter to a photoacoustic gas sensing system.

FIG. 1 illustrates a photoacoustic cell 100 incorporating a quantum dot substrate 116. Photoacoustic cell 100 comprises an excitation source 110 to generate a light spectrum 112, a quantum dot substrate 116 to emit a specific wavelength 113 of radiant energy, a chamber 114 having an outer wall 117, a microphone 118, and a gas permeable wall 120.

Excitation source 110 generates a light spectrum. Excitation source 110 may be selected based on several characteristics including cost, power consumption, and modulation frequency. In an embodiment, excitation source 110 may be an LED, an array of LEDs, or an LED pump. In an alternative embodiment, excitation source 110 may be a laser, or laser diode. Excitation source 110 is typically modulated at a frequency of at least 10 Hz. Excitation source 110 may be modulated at higher frequencies in order decrease the sensitivity of photoacoustic cell 100 to acoustical background noise. In an embodiment, excitation source 110 may be modulated at a frequency between 10 and 100 kHz. In an embodiment, excitation source 110 may be modulated at a frequency between 20 and 40 kHz. In an embodiment, excitation source 110 may be modulated at a frequency of approximately 30 kHz.

Light spectrum 112 is generated by excitation source 110. Light spectrum 112 is selected according to the sensitivity of quantum dot substrate 116. Quantum dots generally absorb light at a shorter wavelength than the wavelength at which they emit light via fluorescence, therefore light spectrum 112 will be selected so as to be below the emission wavelength of quantum dot substrate 116. Light spectrum 112 may be within the spectrum of visible light, but need not be. In an embodiment, light spectrum 112 comprises white light. In an embodiment, light spectrum 112 comprises ultraviolet (UV) light.

Quantum dot substrate 116 is located between the excitation source 110 and a chamber 114, and consists of at least one layer of quantum dots arranged on an optically transparent substrate. Quantum dots emit light via fluorescence. A photon from light spectrum 112 is absorbed by the quantum dots and results in an electron-hole pair. The electron is generated at a relatively high energy state and then relaxes back to the valance band. When this occurs, the electron and hole recombine and emit a photon having a specific wavelength 113 (described below). The overall process converts a photon from light spectrum 112 into a lower energy photon having specific wavelength 113. The specific wavelength of the emitted photon is dictated by the band gap of the quantum dot material, and will be essentially monochromatic for a given quantum dot diameter and material composition.

The quantum dots may comprise lead selenide (PbSe), lead sulfide (PbS), mercury telluride (HgTe), or any combination thereof. Quantum dot substrate 116 may be formed by any suitable means. In an embodiment, quantum dot substrate 116 may be formed by direct printing of quantum dots in a random pattern. In an embodiment, quantum dot substrate 116 may be formed by direct printing of quantum dots in an arranged structure. If desired, a protective layer may be added over the quantum dots to protect them from the environment. In an embodiment, quantum dot substrate 116 may comprise a coating of quantum dots applied to glass and coated with a protective layer.

Quantum dot substrate 116 fluoresces within a narrow band when subjected to the light spectrum 112, and emits a specific wavelength 113 to be received by the chamber 114. The width of the band quantum dot substrate 116 fluoresces in may be tuned through careful selection of the quantum dots used. The quantum dot substrate 116 may comprise quantum dots of a uniform material composition and size to produce a monochromatic IR source, or may comprise quantum dots of varying size and/or composition to produce a complex IR emission spectrum. For example, if it is desirable for quantum dot substrate 116 to fluoresce across a wide band of wavelengths, quantum dots of varying sizes may be used to assemble quantum dot substrate 116. Similarly, if it is desirable for quantum dot substrate 116 to fluoresce across an extremely narrow band, quantum dots having virtually identical sizes may be used to assemble quantum dot substrate 116. In an embodiment, an interchangeable array of quantum dot substrates 116 may be used, each emitting a suitable predetermined specific wavelength 113.

Specific wavelength 113 is emitted by the quantum dot substrate 116. The specific wavelength 113 emitted by quantum dot substrate 116 depends generally on the size and composition of the quantum dots comprising the quantum dot substrate 116, and will be selected according to the particular gas the photoacoustic cell 100 is to detect. Specific wavelength 113 refers to the wavelength at which the peak intensity of the energy emitted by quantum dot substrate 116 occurs. The specific wavelength 113 may be tuned by controlling the geometry of quantum dot substrate 116. In general, depending on the material, smaller quantum dots fluoresce at lower wavelengths (into the visible), whereas larger quantum dots fluoresce in the red and infrared region. For example, a quantum dot substrate 116 assembled from relatively small quantum dots will emit a specific wavelength 113 that is shorter, has higher energy, and is therefore bluer, than a quantum dot substrate 116 assembled from relatively large quantum dots, which would emit a longer, and therefore redder, specific wavelength 113. In an embodiment, quantum dot substrate 116 may comprise quantum dots ranging in size from approximately 2-60 nm.

The specific wavelength 113 should be chosen to broadly coincide with the strongest absorption band of the gas to be detected by photoacoustic cell 100. Typically, the specific wavelength 113 will be in the infrared (IR) band. For example, if photoacoustic cell 100 will be used to detect generic hydrocarbons, the specific wavelength 113 will be chosen to fall within the range of approximately 3.0-3.5 microns. In an embodiment, the specific wavelength 113 emitted by quantum dot substrate 116 may be in the range of 1-4 microns. In an embodiment, the specific wavelength 113 emitted by quantum dot substrate 116 may be in the range of 3-4 microns. Such an embodiment may be used to detect, for example, generic hydrocarbons, methane ($CH_4$), or sulfur dioxide ($SO_2$). In an embodiment, the specific wavelength 113 emitted by the quantum dot substrate 116 may be approximately 3.3 microns, and may be used for detecting methane. In an alternative embodiment, specific wavelength 113 may be approximately 4.0 microns, and may be used for calibrating photoacoustic cell 100.

Chamber 114 receives the specific wavelength 113 emitted by quantum dot substrate 116 and serves as the measurement volume of the photoacoustic cell 100. In an embodiment, chamber 114 may be generally cube-shaped, and may have a volume of approximately one cubic centimeter.

Microphone 118 is sensitive to acoustic signals, and is positioned to detect pressure changes within the chamber 114. Pressure changes within chamber 114 are caused by gases within chamber 114 absorbing the radiant energy of specific wavelength 113 and changing temperature as a result. The temperature fluctuations in the gas track the modulation frequency of specific wavelength 113. Within chamber 114, pressure fluctuations that accompany the temperature fluctuations are detected by microphone 118. Any suitable acoustic transducer may be used. In an embodiment, microphone 118 may comprise an electret microphone. In an alternative embodiment, microphone 118 may comprise a piezoelectric material.

Outer wall 117 of chamber 114 may be constructed of any suitable material. In an embodiment, outer wall 117 may comprise a metal, such as aluminum. In an alternative embodiment, outer wall 117 may comprise a plastic, or polymer, such as methacrylate.

Gas permeable wall 120 may be covered by a porous membrane formed of paper, a porous metal, or a gas permeable polymer. Thus, after photoacoustic cell 100 is located for several minutes within a given environment, the gas mixture within chamber 114 will substantially match the gas mixture of the surrounding environment.

Figure 2:
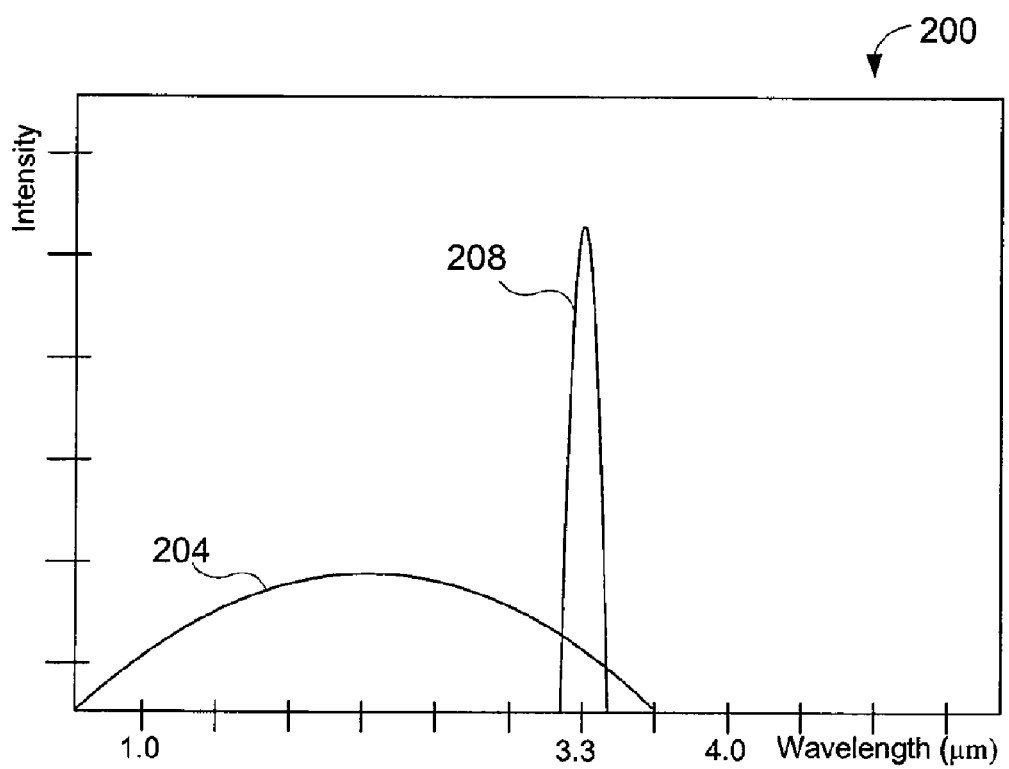
FIG. 2 is a graph indicating wavelength and intensity of light used by a photoacoustic cell, in accordance with an example embodiment of the subject matter.

FIG. 2 illustrates a graph 200 indicating wavelength and intensity of light used by a photoacoustic cell, in accordance with an example embodiment of the subject matter. Graph 200 shows, in an example embodiment, how the light spectrum 112 generated by excitation source 110 may cover a broad range 204 of wavelengths (shown on the x-axis, in microns). Graph 200 also shows that the specific wavelength 113 emitted by quantum dot substrate 116 is within a narrow range 208 of wavelengths in the IR band, and is of a longer wavelength than light spectrum 112.

Figure 3:
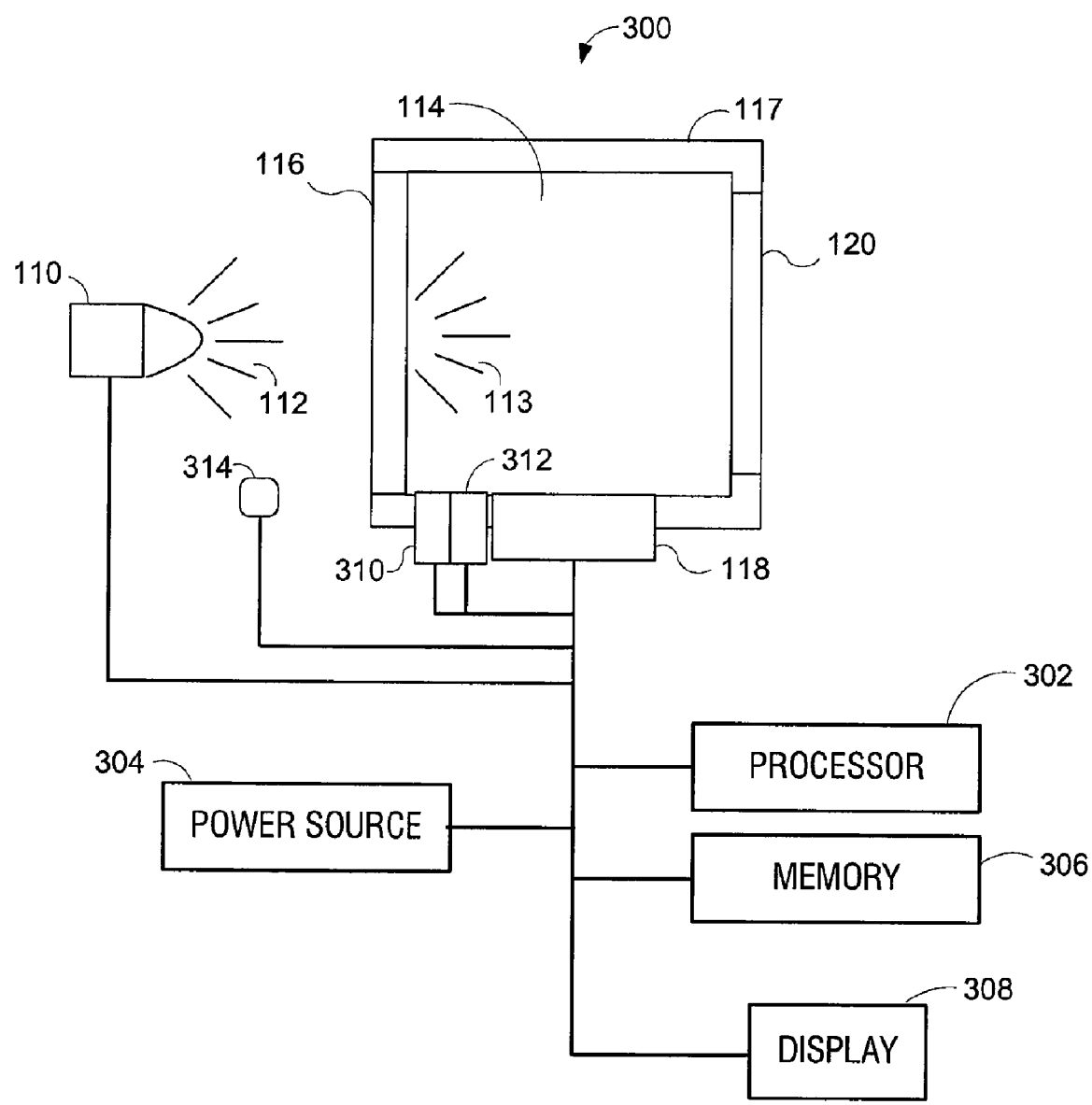
FIG. 3 is a block diagram of a photoacoustic gas sensing system incorporating a quantum dot substrate, according to an example embodiment of the subject matter.

FIG. 3 is a block diagram of a photoacoustic gas sensing system 300 incorporating a quantum dot substrate 116, according to an example embodiment of the subject matter. Photoacoustic gas sensing system 300 comprises an excitation source 110 to generate a light spectrum 112, a quantum dot substrate 116 to generate a specific wavelength 113 of radiant energy, a chamber 114 having an outer wall 117, a gas permeable wall 120, a microphone 118, a temperature sensor 310, a pressure sensor 312, a photodiode 314, a processor 302, a power source 304, a memory 306, and a display 308. Elements 110, 112, 113, 114, 116, 117, 118, and 120 may be identical or similar to the elements described in FIG. 1.

Temperature sensor 310 is coupled to microphone 118. Temperature sensor 310 measures the temperature of microphone 118 in order to generate a correction signal to compensate for temperature induced changes in sensitivity of microphone 118. Any suitable temperature measurement device may be used. In an embodiment, temperature sensor 310 may comprise a thermocouple.

Pressure sensor 312 is coupled to chamber 114. Pressure sensor 312 measures the atmospheric pressure of chamber 114 in order to generate a pressure correction signal. Pressure sensor 312 may be used to compensate for variations in the environment surrounding photoacoustic cell 100. For example, pressure sensor 312 may be used to compensate for changes in barometric pressure caused by a change in altitude or weather conditions. Any suitable pressure measurement device may be used.

Photodiode 314 is located between the excitation source and the quantum dot substrate. Photodiode 314 is positioned to measure the intensity of the light spectrum 112 emitted by excitation source 110. The intensity of the specific wavelength 113 emitted by quantum dot substrate 116 is directly proportional to the intensity of light spectrum 112. Accordingly, in an embodiment, photodiode 314 may be used to monitor the intensity of specific wavelength 113 for purposes of calibrating photoacoustic gas sensing system 300.

Processor 302 receives signals related to pressure changes within chamber 114. Processor 302 is electrically coupled to excitation source 110 and microphone 118. Processor 302 includes circuitry for controlling the modulation of excitation source 110, as well as circuitry for receiving and processing signals from microphone 118, temperature sensor 310, pressure sensor 312, and photodiode 314. Processor 302 performs calculations on the signals to identify the one or more gases within chamber 114 and a concentration corresponding to each of those gases. In an embodiment, processor 302 may comprise a microcontroller. As used herein, "processor" means any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), or any other type of processor or processing circuit.

Memory 306 is used by the processor circuitry during operation, and may include random access memory (RAM), one or more hard drives, and/or one or more drives that handle removable media.

Display 308 indicates the presence and respective concentration values of the particular gases within chamber 114. Display 308 may comprise any suitable output device, including a video terminal, LED indicator, analog gauge, printer, or other peripheral device. Generally, display 308 indicates concentration measures of a particular gas in terms of parts per million (ppm). Display 308 may also be used to indicate the modulation frequency of excitation source 110. In an embodiment, display 308 indicates the concentration value corrected for ambient temperature and pressure. In an alternative embodiment, display 308 comprises an indicator lamp or LED that illuminates when the concentration of a particular gas reaches a predetermined level.

Power source 304 provides power to excitation source 110, microphone 118, temperature sensor 310, pressure sensor 312, processor 302, memory 306, and display 308. In an embodiment, system 300 is portable, and power source 304 may comprise a battery, such as a rechargeable lithium-ion battery. In an alternative embodiment, power source 304 may comprise an alternating current (AC) adaptor.

Figure 4:
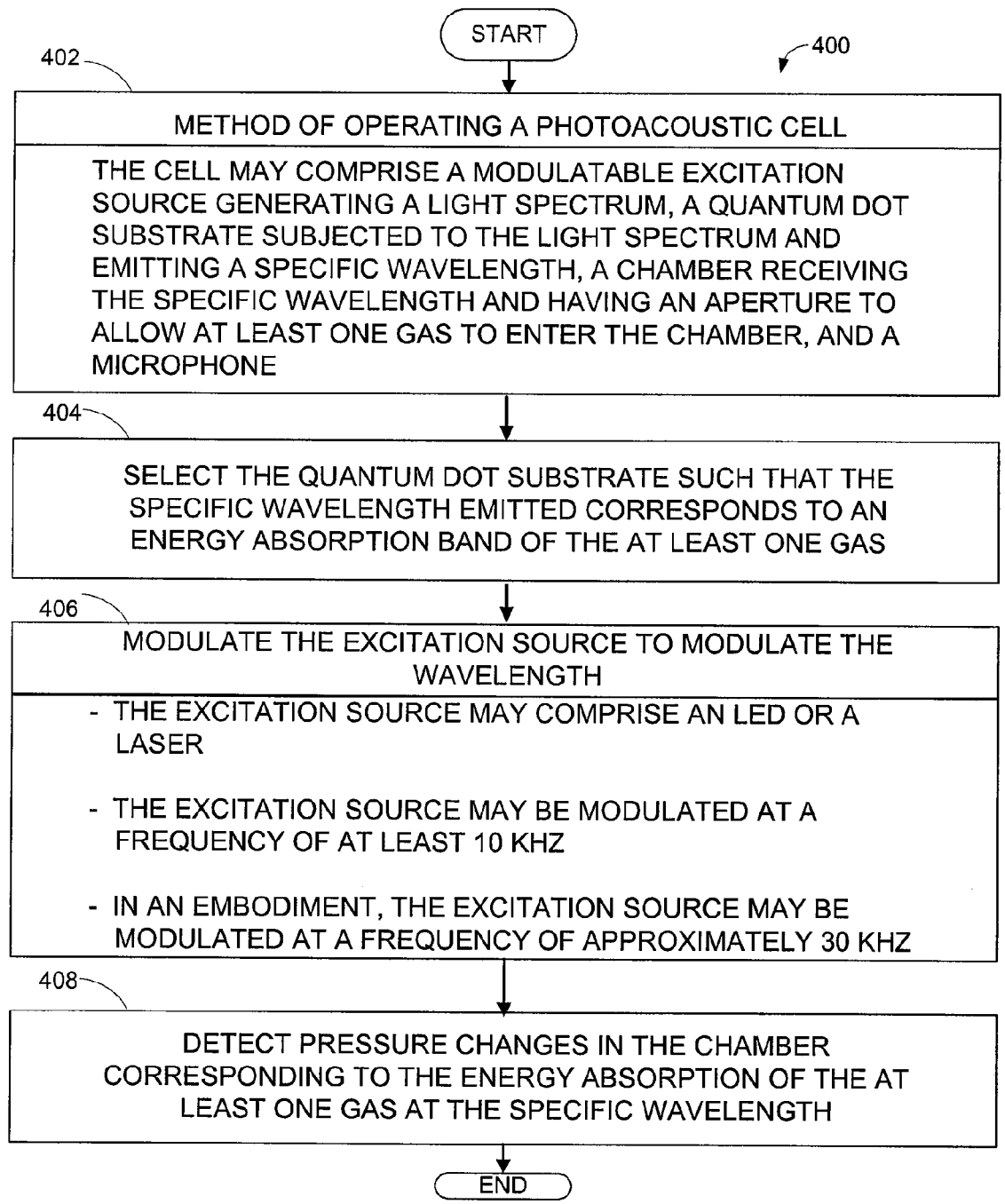
FIG. 4 is a flow diagram of several alternative methods of operating a photoacoustic cell, in accordance with various embodiments of the subject matter.

FIG. 4 is a flow diagram 400 of several alternative methods of operating a photoacoustic cell, in accordance with various embodiments of the subject matter.

In 402, the cell may comprise a modulatable excitation source generating a light spectrum, a quantum dot substrate subjected to the light spectrum and emitting a specific wavelength, a chamber receiving the specific wavelength and having an aperture to allow at least one gas to enter the chamber, and a microphone.

In 404, the quantum dot substrate is selected such that the specific wavelength emitted corresponds to an energy absorption band of the at least one gas. Table 1, below, provides examples of various gases and their corresponding absorption peaks.

TABLE 1

| Gas | Absorption Peak (microns) |
| --- | --- |
| $H_2O$ (water vapor) | 1.4, 1.9 |
| $CH_4$ | 3.3 |
| $SO_2$ | 4.0 |
| $CO_2$ | 4.3 |
| CO | 4.7 |
| NO | 5.3 |

Generally, when assembling the photoacoustic cell, it will be known what particular gas the cell will be used to detect. Therefore, in selecting the quantum dot substrate, one need only determine a unique absorption band of the particular gas, i.e. an absorption band that is not shared with other gases, and select a quantum dot substrate with a similar emission peak. If it is desired to detect multiple gases, an interchangeable array of quantum dot substrates may be used, each emitting a different wavelength corresponding to the absorption peak of a different gas. As discussed above, the emission peak of the quantum dot substrate is predominately a function of the size and composition of the quantum dots.

In 406, the excitation source is modulated to modulate the specific wavelength. In an embodiment, the excitation source may comprise an LED or a laser. In an embodiment, the excitation source may be modulated at a frequency of at least 10 kHz. In an embodiment, the excitation source may be modulated at a frequency of approximately 30 kHz. The light spectrum generated by the excitation source may be white light. The light spectrum is chosen based on the properties of the selected quantum dot substrate, particularly the peak emission wavelength, as the sensitivity of the quantum dot substrate to the light spectrum may vary with different quantum dot geometries and sizes.

In 408, pressure changes in the chamber are detected that correspond to the energy absorption of the at least one gas at the specific wavelength. These pressure changes will occur at the modulation frequency of the excitation source, and will vary in intensity according to the concentration of the gas. Pressure changes are detected and converted to an electrical signal by a microphone. The microphone may be a low cost electret type. A processor then performs calculations on the microphone signal, allowing the presence and concentration of a particular gas to be determined. The concentration of the gas may be displayed, or may be used to trigger an alarm if greater than a predetermined level.

Other embodiments will be readily apparent to those of ordinary skill in the art after reading this disclosure.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the subject matter. Therefore, it is manifestly intended that embodiments of the subject matter be limited only by the claims and the equivalents thereof.

It is emphasized that the Abstract is provided to comply with 37 C.F.R. §1.72(b) requiring an Abstract that will allow the reader to ascertain the nature and gist of the technical disclosure. It is submitted with the understanding that it will not be used to interpret or limit the scope or meaning of the claims.

In the foregoing Detailed Description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

What is claimed is:

1. A photoacoustic cell comprising:
   an excitation source to generate a light spectrum;
   a chamber;
   a quantum dot substrate located between the excitation source and the chamber; and forming a wall of the chamber, the quantum dot substrate, when subjected to the light spectrum, to emit a specific wavelength to be received by the chamber;
   a microphone positioned to detect pressure changes within the chamber.

2. The photoacoustic cell of claim 1, wherein the excitation source comprises a light emitting diode.

3. The photoacoustic cell of claim 1, wherein the excitation source comprises a laser.

4. The photoacoustic cell of claim 1, wherein the excitation source is modulated at a frequency between 20 and 40 kilohertz.

5. The photoacoustic cell of claim 1, wherein the chamber comprises at least one gas permeable wall.

6. The photoacoustic cell of claim 1, wherein the specific wavelength emitted by the quantum dot substrate is 3.3 microns.

7. A photoacoustic gas sensing system comprising:
   an excitation source to generate a light spectrum;
   a chamber;
   a quantum dot substrate located between the excitation source and the chamber and forming a wall of the chamber, the quantum dot substrate, when subjected to the light spectrum, to emit a specific wavelength to be received by the chamber;
   a microphone positioned to generate a signal related to pressure changes within the chamber;
   a temperature sensor coupled to the microphone to measure a temperature of the microphone;
   a processor, to receive the signal, electrically coupled to the excitation source and the microphone, the processor to perform calculations on the signal to identify one or more gases within the chamber and a concentration corresponding to each of the one or more gases; and
   a power source to provide power to at least the excitation source, the microphone, and the processor.

8. The photoacoustic gas sensing system of claim 7, and further comprising a display coupled to the processor, the display to indicate a concentration value of the one or more gases within the chamber.

9. The photoacoustic gas sensing system of claim 7, wherein the excitation source comprises a light emitting diode.

10. The photoacoustic gas sensing system of claim 7, wherein the excitation source comprises a laser.

11. The photoacoustic gas sensing system of claim 7, wherein the excitation source is modulated at a frequency between 10 and 100 kilohertz.

12. The photoacoustic gas sensing system of claim 7, wherein the chamber comprises at least one gas permeable wall.

13. The photoacoustic gas sensing system of claim 7, wherein the specific wavelength emitted by the quantum dot substrate is in the range of 3 to 4 microns.

14. A photoacoustic gas sensing system comprising:
   an excitation source to generate a light spectrum;
   a chamber;
   a quantum dot substrate located between the excitation source and the chamber, the quantum dot substrate, when subjected to the light spectrum, to emit a specific wavelength to be received by the chamber;
   a microphone positioned to generate a signal related to pressure changes within the chamber;
   a processor, to receive the signal, electrically coupled to the excitation source and the microphone, the processor to perform calculations on the signal to identify one or more gases within the chamber and a concentration corresponding to each of the one or more gases;
   a power source to provide power to at least the excitation source, the microphone, and the processor; and
   a photodiode located between the excitation source and the quantum dot substrate, the photodiode to measure the intensity the light spectrum.

15. A method of operating a photoacoustic cell, wherein the cell comprises a modulatable excitation source generating a light spectrum, a quantum dot substrate subjected to the light spectrum and emitting a specific wavelength, a chamber receiving the specific wavelength and having an aperture to allow at least one gas to enter the chamber, and a microphone, the method comprising:

modulating the excitation source to modulate the specific wavelength;

measuring the light spectrum between the excitation source and the quantum dot substrate;

measuring a temperature of the microphone; and detecting pressure changes in the chamber corresponding to the energy absorption of one of the at least one gases at the specific wavelength.

16. The method of claim 15, further comprising selecting the quantum dot substrate such that the specific wavelength emitted corresponds to an energy absorption band of the at least one gas.

17. The method of claim 15, wherein the modulatable excitation source comprises at least one light emitting diode.

18. The method of claim 15, wherein the modulatable excitation source comprises a laser.

19. The method of claim 15, wherein modulating the excitation source comprises modulating it at a frequency of at least 10 kilohertz.

20. The method of claim 15, wherein the specific wavelength emitted by the quantum dot substrate is in the range of 1 to 4 microns.

* * * * *